(12) United States Patent
Indani et al.

(10) Patent No.: US 12,399,174 B2
(45) Date of Patent: Aug. 26, 2025

(54) DETECTION OF PATHOGENS FROM A GASEOUS MIXTURE ASSOCIATED WITH SECRETIONS

(71) Applicant: Tata Consultancy Services Limited, Mumbai (IN)

(72) Inventors: Ashish Indani, Mumbai (IN); Devraj Goulikar, Mumbai (IN); Sanjay Madhukar Kimbahune, Thane (IN); Sai Tanishq Nannapaneni, Hyderabad (IN)

(73) Assignee: Tata Consultancy Services Limited, Mumbai (IN)

( * ) Notice: Subject to any disclaimer, the term of this patent is extended or adjusted under 35 U.S.C. 154(b) by 604 days.

(21) Appl. No.: 17/759,997

(22) PCT Filed: Mar. 26, 2021

(86) PCT No.: PCT/IB2021/052512
§ 371 (c)(1),
(2) Date: Aug. 2, 2022

(87) PCT Pub. No.: WO2021/191849
PCT Pub. Date: Sep. 30, 2021

(65) Prior Publication Data
US 2023/0064209 A1    Mar. 2, 2023

(30) Foreign Application Priority Data
Mar. 27, 2020   (IN) .............................. 202021013505

(51) Int. Cl.
*G01N 33/543*    (2006.01)
*G01N 33/497*    (2006.01)
*G01N 33/569*    (2006.01)

(52) U.S. Cl.
CPC ..... *G01N 33/54373* (2013.01); *G01N 33/497* (2013.01); *G01N 33/569* (2013.01)

(58) Field of Classification Search
CPC ........ G16H 10/40; G16H 40/40; G16H 50/80; G16B 15/30; G01N 2333/005;
(Continued)

(56) References Cited

U.S. PATENT DOCUMENTS

2003/0157498 A1    8/2003   Eyre et al.
2005/0250141 A1    11/2005  Lambert et al.
(Continued)

OTHER PUBLICATIONS

Amiri, Mandana et al., "Electrochemical Methodologies for the Detection of Pathogens", HAL Open Science, Jul. 19, 2019, 43 pages, https://hal.archives-ouvertes.fr/hal-02189343.
(Continued)

*Primary Examiner* — Jennifer Wecker
(74) *Attorney, Agent, or Firm* — Finnegan, Henderson, Farabow, Garrett & Dunner, LLP

(57) ABSTRACT

This disclosure relates generally to detection of pathogens from a gaseous mixture associated with secretions. Conventional methods typically involve invasive or biohazardous techniques, the requirement of quantity limits utility of several natural secretions, there is a dependency on immunological reactions to develop in a subject being monitored resulting in long time taken for detecting pathogens, which increases risk to health and environment. There is also reduced specificity and sensitivity considering the dependency on signature identification or training of machine learning models. Again, prior art focusses on designing antibodies for a particular type of sensor which is challenging when dealing with natural immunoglobulin. The present disclosure addresses these challenges by enabling identification of a most viable sensor for the natural immunoglobin, the viability being based on mathematical representations of
(Continued)

the relationship between a sensor and the immunoglobulin using an ontology of domain knowledge associated with pathogens, technology, processing and detection.

20 Claims, 6 Drawing Sheets

(58) Field of Classification Search
CPC ....... G01N 2333/165; G01N 2333/195; G01N 2469/10; G01N 33/497; G01N 33/4975; G01N 33/543; G01N 33/54373; G01N 33/569; G01N 33/56911; G01N 33/56983; G01N 33/6893
See application file for complete search history.

(56) References Cited

U.S. PATENT DOCUMENTS

| | | |
|---|---|---|
| 2013/0217598 A1 | 8/2013 | Ludwig et al. |
| 2016/0033494 A1 | 2/2016 | Lowery, Jr. et al. |
| 2019/0041394 A1 | 2/2019 | Chen et al. |
| 2020/0333338 A1* | 10/2020 | Kori ............... G01N 33/553 |

OTHER PUBLICATIONS

Byrne, Barry et al., "Antibody-Based Sensors: Principles, Problems and Potential for Detection of Pathogens and Associated Toxins", Sensors 2009, vol. 9, pp. 4407-4445; www.mdpi.com/journal/sensors.

Udugama, Buddhisha et al., "Diagnosing COVID-19: The Disease and Tools for Detection", ACS NANO 2020, vol. 14, pp. 3822-3835, www.acsnano.org.

Fronczek, Christopher F. et al., "Biosensors for Monitoring Airborne Pathogens", Journal of Laboratory Automation, 2015, vol. 20(4), pp. 390-410.

Wujcik, E.K. et al., "Antibody nanosensors: A detailed review", The Royal Society of Chemistry 2014, vol. 4, pp. 43725-43745, www.rsc.org/advances.

International Search Report and Written Opinion mailed Aug. 26, 2021 in International Application No. PCT/IB2021/052512; 10 pages.

* cited by examiner

DETECTION OF PATHOGENS FROM A GASEOUS MIXTURE ASSOCIATED WITH SECRETIONS

PRIORITY CLAIM

The present application is a U.S. National Stage Filing under 35 U.S.C. § 371 and claims priority from International Application No. PCT/IB2021/052512 filed on 26 Mar. 2021, which application claims priority under 35 U.S.C. § 119 from India Application No. 202021013505, filed on Mar. 27, 2020. The entire contents of the aforementioned applications are incorporated herein by reference.

TECHNICAL FIELD

The disclosure herein generally relates to detecting pathogens, and, more particularly, to detecting pathogens from a gaseous mixture associated with secretions.

BACKGROUND

There are two variants of pathogen detection in the state-of-the-art. In a first variant, the conventional methods detect the pathogen, or the antibodies developed by the body against the pathogen. This technique uses immunochemical reactions for conventional detection of the pathogens in any body secretions or the antibodies against antigens in the blood or serum. This technique has high sensitivity and specificity. However, handling the sample in a state other than liquid is a major challenge in this method. These conventional methods for pathogen detection are time consuming to produce confirmed results since they depend upon immunological reactions to develop. The state-of-the-art detection methods are also associated with risk of handling, transportation, error, and disposal leading to vicarious infections. Dependency on medical or paramedical skills and need for a clinical or laboratory set up can prove to be an impediment especially during trying situations like a pandemic.

A second variant of the method of diagnosis or screening includes the identification of pathogens with nanotechnology or microelectronics technology with chemical or any other unique signature identification, with use of artificial intelligence in these devices. These devices can work in various states like liquid, gaseous or semisolid. However, due to dependency on signature identification or training of machine learning (ML) models for confirmation, reduced specificity and sensitivity of this method, limits its practical utility and dependency.

SUMMARY

Embodiments of the present disclosure present technological improvements as solutions to one or more of the above-mentioned technical problems recognized by the inventors in conventional systems.

In an aspect, there is provided a processor implemented method comprising the steps of: determining, via one or more hardware processors, one or more viable sensors to detect a pathogen corresponding to a condition or a disease; the step of determining comprising: performing iteratively, via the one or more hardware processors, on each sensor from a plurality of sensors the followings steps: estimating an amount Q of an antibody to be coated on a surface of a sensor, based on surface area A of the sensor, an average area $\alpha$ of the sensor, and a thickness T of coat on the sensor; determining a sensor specific antibody characterisation factor X of the antibody based on the estimated amount Q of the antibody, technical inputs of the sensor and one or more properties x of the antibody; determining a null threshold $\emptyset$ as a maximum functional propensity value of the sensor beyond which the sensor is falsely activated; determining a sensitivity of the sensor represented by a minimum quantity $Q_{ag}$ of an antigen required for neutralisation of the estimated amount Q of antibody based on (i) a titration factor R between the antibody and the antigen and (ii) the amount Q of antibody; determining quantity $Q_s$ of a substrate required to detect the pathogen, the quantity $Q_s$ of the substrate being based on (i) the minimum quantity $Q_{ag}$ of the antigen, (ii) concentration C−ag of the antigen in the substrate, (iii) the one or more properties x of the antibody, and (iv) the titration factor R representing the amount of the antibody that neutralizes the concentration C−ag of the antigen in the substrate; and comparing the determined quantity $Q_s$ of substrate with the determined null threshold Ø to determine if the sensor is viable to detect the pathogen corresponding to the condition or the disease.

In another aspect, there is provided a system comprising: one or more data storage devices operatively coupled to one or more hardware processors via the one or more input/output interfaces and configured to store instructions configured for execution via the one or more hardware processors to: determine one or more viable sensors to detect a pathogen corresponding to a condition or a disease, by performing iteratively on each sensor from a plurality of sensors, the followings steps: estimating, an amount Q of an antibody to be coated on a surface of a sensor, based on surface area A of the sensor, an average area $\alpha$ of the sensor, and a thickness T of coat on the sensor; determining, a sensor specific antibody characterisation factor X of the antibody based on the estimated amount Q of the antibody, technical inputs of the sensor and one or more properties x of the antibody; determining, a null threshold Ø as a maximum functional propensity value of the sensor beyond which the sensor is falsely activated; determining, a minimum quantity $Q_{ag}$ of an antigen required for neutralisation of the estimated amount Q of antibody based on (i) a titration factor R between the antibody and the antigen and (ii) the amount Q of antibody; determining, quantity $Q_s$ of a substrate required to detect the pathogen, the quantity $Q_s$ of the substrate being based on (i) the minimum quantity $Q_{ag}$ of the antigen, (ii) concentration C−ag of the antigen in the substrate, (iii) one or more properties x of the antibody, and (iv) the titration factor R representing the amount of the antibody that neutralizes the concentration C−ag of the antigen in the substrate; and comparing the determined quantity $Q_s$ of substrate with the determined null threshold Ø to determine if the sensor is viable to detect the pathogen corresponding to the condition or the disease.

In accordance with an embodiment of the present disclosure, the one or more hardware processors are configured to obtain, prior to determining the one or more viable sensors, an ontology of a plurality of inputs comprising: a) pathogen-oriented inputs including: inputs pertaining to a plurality of antigens, each antigen in the plurality of antigens being a target antigen corresponding to the condition or the disease; and inputs pertaining to a plurality of antibodies, each antibody in the plurality of antibodies corresponding to a target antigen in the plurality of antigens; b) technology-oriented inputs including: inputs related to a functional principle of a technology that activates a sensor from the plurality of sensors; and technical inputs of each sensor from the plurality of sensors; c) processing-oriented inputs pertaining to each antibody from the plurality of antibodies and each sensor from the plurality of sensors; and d) detection-oriented inputs pertaining to detection of the pathogen.

In accordance with an embodiment of the present disclosure, the one or more hardware processors are further configured to select a sensor from the determined one or more viable sensors by: iteratively mapping the functional principle of the technology to (i) each sensor from the plurality of sensors, (ii) surface area of an associated sensor, (ii) material of the associated sensor and (iii) the sensitivity of the associated sensor; and selecting the sensor having a highest rank by applying a filtering method, in the event that more than one sensor from the plurality of sensors are selected based on the iterative mapping. Optionally, further mapping with a binding material for binding the antibody to the sensor may be considered.

In accordance with an embodiment, the system described above, may further comprise: a gas collection unit configured to collect the gaseous mixture associated with a secretion, wherein the secretion is the substrate for the pathogen; a sensor being the selected sensor coated with the estimated amount of the antibody corresponding to the target antigen that further corresponds to the condition or the disease; and wherein the one or more hardware processors are configured to detect the pathogen in the collected gaseous mixture based on an outcome of a reaction between the antigen and the antibody.

In accordance with an embodiment of the present disclosure, the one or more hardware processors are further configured to quantify the detected pathogen based on a quantum of the outcome of the reaction between the antigen and the antibody using (i) the minimum quantity $Q_{ag}$ of the antigen required for neutralisation of the estimated amount of antibody and result in an outcome and (ii) a maximum quantity of the antigen beyond which the outcome does not change.

In accordance with an embodiment of the present disclosure, the one or more hardware processors are further configured to include one or more of: a preprocessor configured to preprocess the collected gaseous mixture received via the gas collection unit such that the pathogen contained in the collected gaseous mixture is released; and a display configured to provide the outcome indicative of at least one of (i) the presence or absence of the pathogen and (ii) quantitative information of the detected pathogen.

In another embodiment, there is provided a device for detecting a pathogen corresponding to a condition or a disease, the device comprising: a gas collection unit configured to collect a gaseous mixture associated with a secretion, wherein the secretion is the substrate for the pathogen; a sensor coated with an estimated amount of an antibody corresponding to a target antigen that further corresponds to the condition or the disease; wherein the pathogen in the collected gaseous mixture is detected based on an outcome of a reaction between the target antigen and the antibody.

In an embodiment, the device described above may include one or more of: a preprocessor configured to preprocess the collected gaseous mixture received via the gas collection unit such that the pathogen contained in the collected gaseous mixture is released; and a display configured to provide the outcome indicative of at least one of (i) the presence or absence of the pathogen and (ii) quantitative information of the detected pathogen.

In yet another aspect, there is provided a computer program product comprising a non-transitory computer readable medium having a computer readable program embodied therein, wherein the computer readable program, when executed on a computing device, causes the computing device to: determine one or more viable sensors to detect a pathogen corresponding to a condition or a disease, by performing iteratively on each sensor from a plurality of sensors, the followings steps: estimating, an amount Q of an antibody to be coated on a surface of a sensor, based on surface area A of the sensor, an average area $\alpha$ of the sensor, and a thickness T of coat on the sensor; determining, a sensor specific antibody characterisation factor X of the antibody based on the estimated amount Q of the antibody, technical inputs of the sensor and one or more properties x of the antibody; determining, a null threshold Ø as a maximum functional propensity value of the sensor beyond which the sensor is falsely activated; determining, a minimum quantity $Q_{ag}$ of an antigen required for neutralisation of the estimated amount Q of antibody based on (i) a titration factor R between the antibody and the antigen and (ii) the amount Q of antibody; determining, quantity $Q_s$ of a substrate required to detect the pathogen, the quantity $Q_s$ of the substrate being based on (i) the minimum quantity $Q_{ag}$ of the antigen, (ii) concentration C−ag of the antigen in the substrate, (iii) the one or more properties x of the antibody, and (iv) the titration factor R representing the amount of the antibody that neutralizes the concentration C−ag of the antigen in the substrate; and comparing the determined quantity $Q_s$ of substrate with the determined null threshold Ø to determine if the sensor is viable to detect the pathogen corresponding to the condition or the disease.

In an embodiment, the computer readable program further causes the computing device to obtain, prior to determining the one or more viable sensors, an ontology of a plurality of inputs comprising: a) pathogen-oriented inputs including: inputs pertaining to a plurality of antigens, each antigen in the plurality of antigens being a target antigen corresponding to the condition or the disease; and inputs pertaining to a plurality of antibodies, each antibody in the plurality of antibodies corresponding to a target antigen in the plurality of antigens; b) technology-oriented inputs including: inputs related to a functional principle of a technology that activates a sensor from the plurality of sensors; and technical inputs of each sensor from the plurality of sensors; c) processing-oriented inputs pertaining to each antibody from the plurality of antibodies and each sensor from the plurality of sensors; and d) detection-oriented inputs pertaining to detection of the pathogen.

In an embodiment, the computer readable program further causes the computing device to select a sensor from the determined one or more viable sensors by: iteratively mapping the functional principle of the technology to (i) each sensor from the plurality of sensors, (ii) surface area of an associated sensor, (ii) material of the associated sensor and (iii) the sensitivity of the associated sensor; and selecting the sensor having a highest rank by applying a filtering method, in the event that more than one sensor from the plurality of sensors are selected based on the iterative mapping. Optionally, further mapping with a binding material for binding the antibody to the sensor may be considered.

In an embodiment, the computer readable program further causes the computing device to quantify the detected pathogen based on a quantum of the outcome of the reaction between the antigen and the antibody using (i) the minimum quantity $Q_{ag}$ of the antigen required for neutralisation of the estimated amount of antibody and result in an outcome and (ii) a maximum quantity of the antigen beyond which the outcome does not change.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION OF EMBODIMENTS

Figure 1:
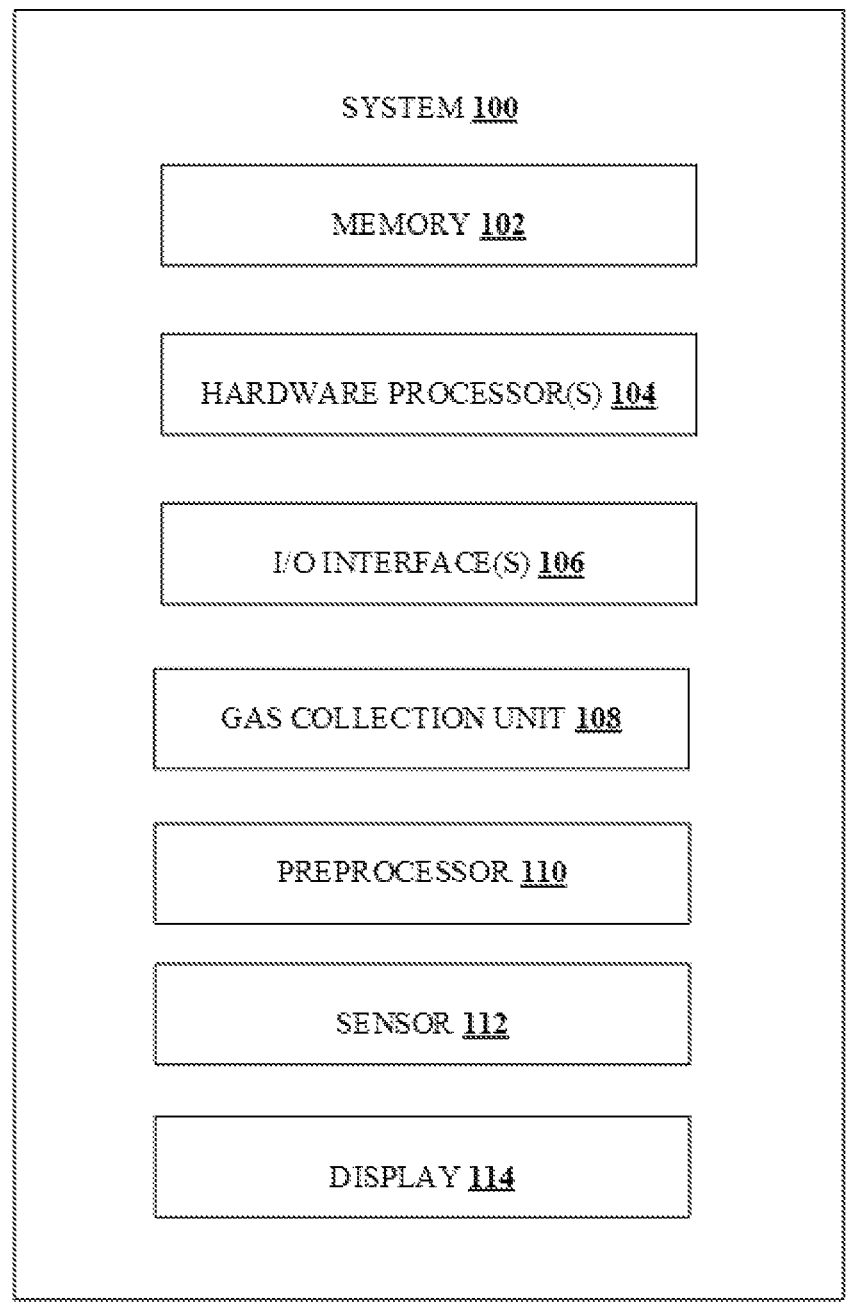
FIG. 1 is a high-level block diagram of a system for detection of pathogens from a gaseous mixture associated with secretions, according to some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following embodiments described herein.

Conventional methods and devices for detecting pathogens typically involve invasive or biohazardous techniques like collection of blood by phlebotomy or deep nasal swab collection or collection of urine sample in a specific type of container in a significant quantity that may remain as a biological hazard. In addition, the requirement of quantity limits utility of several natural secretions like tears, nasal discharge, droplet or droplet nuclei present in the breath or cough. Further, the conventional methods depend upon immunological reactions to develop in a subject being monitored. Hence, time taken for detecting pathogens, if any, is long, which may be detrimental to the subject's health and environment in some scenarios. Besides the time taken, need for medical experts and clinical setups may pose a practical challenge during trying scenarios such as pandemics or spread of contagions when human and infrastructural resources may be limited considering the volume of subjects to be monitored. Some of the conventional methods also have limitations in terms detection of newer strains of the pathogen considering their dependency on signature identification for detecting pathogens. In addition, detection of the pathogen in animals other than human and domestic pet animals is another challenge considering a substrate collection aspect.

Again, prior art focusses on designing antibodies for a particular type of sensor. However, this approach is challenging when dealing with natural immunoglobulin since the antibody cannot be customized or designed. The method and device of the present disclosure aims to address these challenges by selecting a most viable sensor for the natural immunoglobin. Another challenge with the art addressed in the present disclosure relates to identification of bacterial toxins rather than the bacteria itself. Presence of toxins does not necessarily represent presence of the associated bacteria leading to erroneous findings.

In the context of the present disclosure, the expression 'secretion' may refer to natural secretions including sweat, urine, tears, saliva, feces, breath, milk, respiratory tract secretions, genital secretions like semen or vaginal discharges, and the like. In some embodiments, the expression 'secretions' may also include pathological secretions like pus, sputum, nasal discharge, vomitus, flatus, the air blown over the clothes, body, discarded dressings, and the like. The secretions used in accordance with the present disclosure may be obtained in their routine disposal state. In addition, the method of the present disclosure can work with blood, serum or any such intentionally collected samples. For instance, during pre-operative checks, the method and system of the present disclosure may be employed in stead of exposing a laboratory to a potential risk, if any.

In the context of the present disclosure, the expression 'pathogen' may refer to an antigen or a hapten that is capable of stimulating an immune response. Accordingly, 'pathogen' may be a microbe (bacterium, virus, or other disease-causing microorganism, and the like) or pollen, dust, dust-mite, parts of insects of some organisms, and the like, that may be transmitted via a 'gaseous mixture' like steam, fumes, dispersion or aerosol state of the liquids and like. For the sake of simplicity, the expressions 'antigen' and 'pathogen' may be used interchangeably.

Likewise, in the context of the present disclosure, the expression 'gaseous mixture' may include pathogens capable of transmission that is airborne or is present in droplet, droplet nucleus, fumes, vapor, sublimate, dispersion, smoke, soot, or any other created aerosol form with heating or cooling of a liquid, or solid materials to fumes, vapors, sublimate, etc. of the materials that can cause a disease or a condition.

Furthermore, in the context of the present disclosure, the expression 'sensors' represent typically nanosensors and microsensors.

Referring now to the drawings, and more particularly to FIG. 1 through FIG. 4, where similar reference characters denote corresponding features consistently throughout the figures, there are shown preferred embodiments and these embodiments are described in the context of the following exemplary system and/or method.

FIG. 1 is a high-level block diagram of a system 100 for detection of pathogens from a gaseous mixture associated with secretions, according to some embodiments of the present disclosure. In an embodiment, the system 100 includes one or more hardware processors 104, communication interface device(s) or input/output (I/O) interface(s) 106, and one or more data storage devices or memory 102 operatively coupled to the one or more hardware processors 104. The one or more hardware processors 104 can be implemented as one or more microprocessors, microcomputers, microcontrollers, digital signal processors, central processing units, state machines, graphics controllers, photo-activation units, logic circuitries, and/or any devices that manipulate signals based on operational instructions. Among other capabilities, the processor(s) are configured to fetch and execute computer-readable instructions stored in the memory. In the context of the present disclosure, the expressions 'processors' and 'hardware processors' may be used interchangeably. In an embodiment, the system 100 can be implemented in a variety of computing systems, such as laptop computers, notebooks, hand-held devices, workstations, mainframe computers, servers, a network cloud and the like.

I/O interface(s) 106 can include a variety of software and hardware interfaces, for example, a web interface, a graphical user interface, a digital-electronic communication like near field communication, Bluetooth®, Internet of Things, General Packet Radio Service (GPRS), and the like and can facilitate multiple communications within a wide variety of networks N/W and protocol types, including wired networks, for example, LAN, cable, etc., and wireless networks, such as WLAN, cellular, or satellite. In an embodiment, the I/O interface(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, one or more modules of the system 100 can be stored in the memory 102.

In an embodiment, the system 100 includes a gas collection unit 108, a preprocessor 110, a sensor 112, and a display 114. In accordance with the present disclosure, one or more components of the system 100 may be disposable to avert cross contamination or false positive reactions, while one or more components may be configured such that they are recyclable. In an embodiment, the system 100 may itself be a disposable device. In an embodiment, one or more components of the system 100 may be configured to be external to the system 100. In an embodiment, the components of the system 100 are integrated to form a single unit.

In an embodiment, the gas collection unit 108 may be a sterile tubular chamber configured to receive a gaseous mixture for analyses. For instance, when considering a secretion associated with say breath or cough, a subject may exhale into the gas collection unit 108. In an embodiment, the gaseous mixture may be pumped into the gas collection unit 108. However, the gas collection unit may be implemented in different forms such as a vacuuming blower, locked bag, mask or vaporizer etc. or can work with some traditional collection methods like swab, or finger prick etc. However, the major difference in the collection requirements is about the quantity of the sample required, which usually is a few milliliters in traditional methods versus a 1-10 microliters in the method described in this disclosure In an embodiment of the present disclosure, the preprocessor 110 is configured to preprocess the gaseous mixture received via the gas collection unit 108 such that the pathogens contained therein are released. In an embodiment, the preprocessor may be a heater, a cooler, a fumigator, a compactor, and the like. In some scenarios, pre-processing may involve condensation, formation of gel or solution by passing through a liquid, etc. The air collected by vacuum blower over clothes or body may require to go through a process of pre-compression to increase the concentration of the pathogens in the given samples. In an exemplary embodiment, in the case of a droplet nuclei contained in the gaseous mixture of say, human breath, the preprocessor 110 may be a heater configured to release the pathogen from water content in the droplet nuclei. The preprocessor 110 may be an optional component needed for certain applications involving say the droplet nuclei. When airborne transmission is considered, there may not be a need for the preprocessor 110 and the received gaseous mixture via the gas collection unit 108 may directly be processed by the sensor 112.

In accordance with an embodiment of the present disclosure, the sensor 112 may be, but not limited to a Micro Electro Mechanical System (MEMS) sensor, an electromagnetic sensor, a photoelectric sensor, a chemical sensor, a photo-caloric sensor like fluorescence, a photometric sensor like change in spectrum, etc., in the form of say, cantilevers, nanochips, electrodes, sensor strips, and the like. Particularly, in accordance with the present disclosure, the sensor 112 is coated with an estimated amount of antibody corresponding to a target antigen that further corresponds to the condition or the disease under observation and is configured to be activated by an antigen-antibody reaction. The antibody may be provided by techniques like coating, compounding, chemical plating, chain-reaction based binding, electroplating, and the like.

To understand target antigen, consider COVID-19 virus. There are over 200 different proteins in a coronavirus, of which a few surface proteins and a few nucleocapsid proteins are specific to the COVID-19 virus. These specific proteins which are identified as Spike-1 (S1) and Spike-2 (S2) proteins and neucleocapsid-1 (NP1) proteins are specific antigens which are the targets on the pathogen "novel CoronaVirus" for its identification. These proteins are referred to as target antigens.

In accordance with an embodiment of the present disclosure, the display 114 is configured to provide an outcome generated by the sensor upon being activated by the antigen-antibody reaction indicative of the presence or absence of the pathogen. In an embodiment, the display may provide a binary response such as positive or negative. In another embodiment, the display may provide a quantitative information associated with the detected pathogen in the form of say concentration of the detected pathogen. In an exemplary embodiment, the sensor may be activated by the antigen-antibody reaction to detect breath pathogen and display information associated with say corona virus indicative of Severe Acute Respiratory Syndrome (SARS), Middle East respiratory syndrome (MERS), Corona Virus Disease 2019 (COVID-19), virus indicative of Ebola, Zica, influenza, Anthrax, or bacteria indicative of Tuberculosis, Pneumococcus, and the like.

Figure 2A:
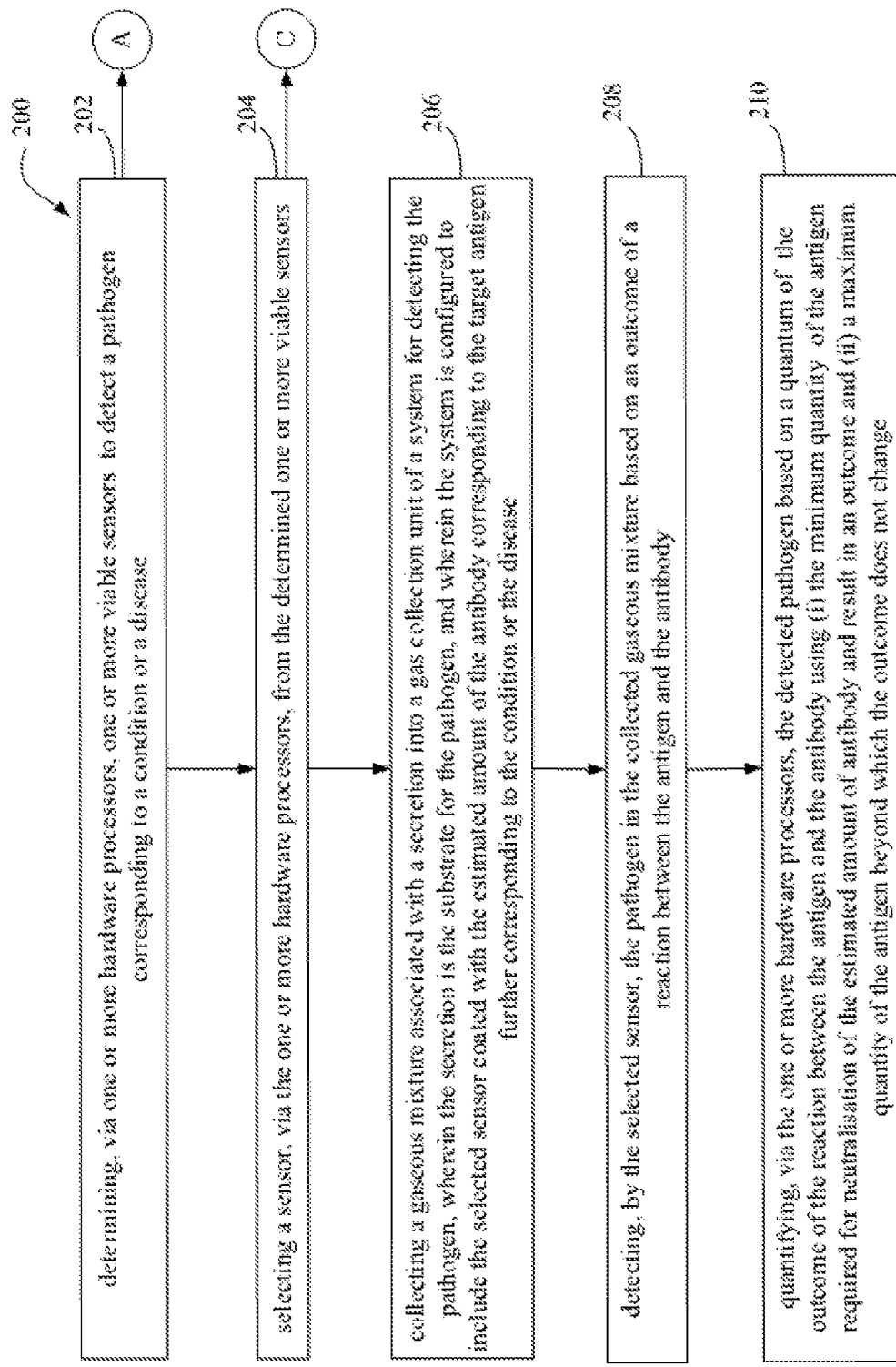
FIG. 2A through FIG. 2C illustrates an exemplary flow diagram of a computer implemented method for detection of pathogens from a gaseous mixture associated with secretions, in accordance with some embodiments of the present disclosure.
Figure 2B:
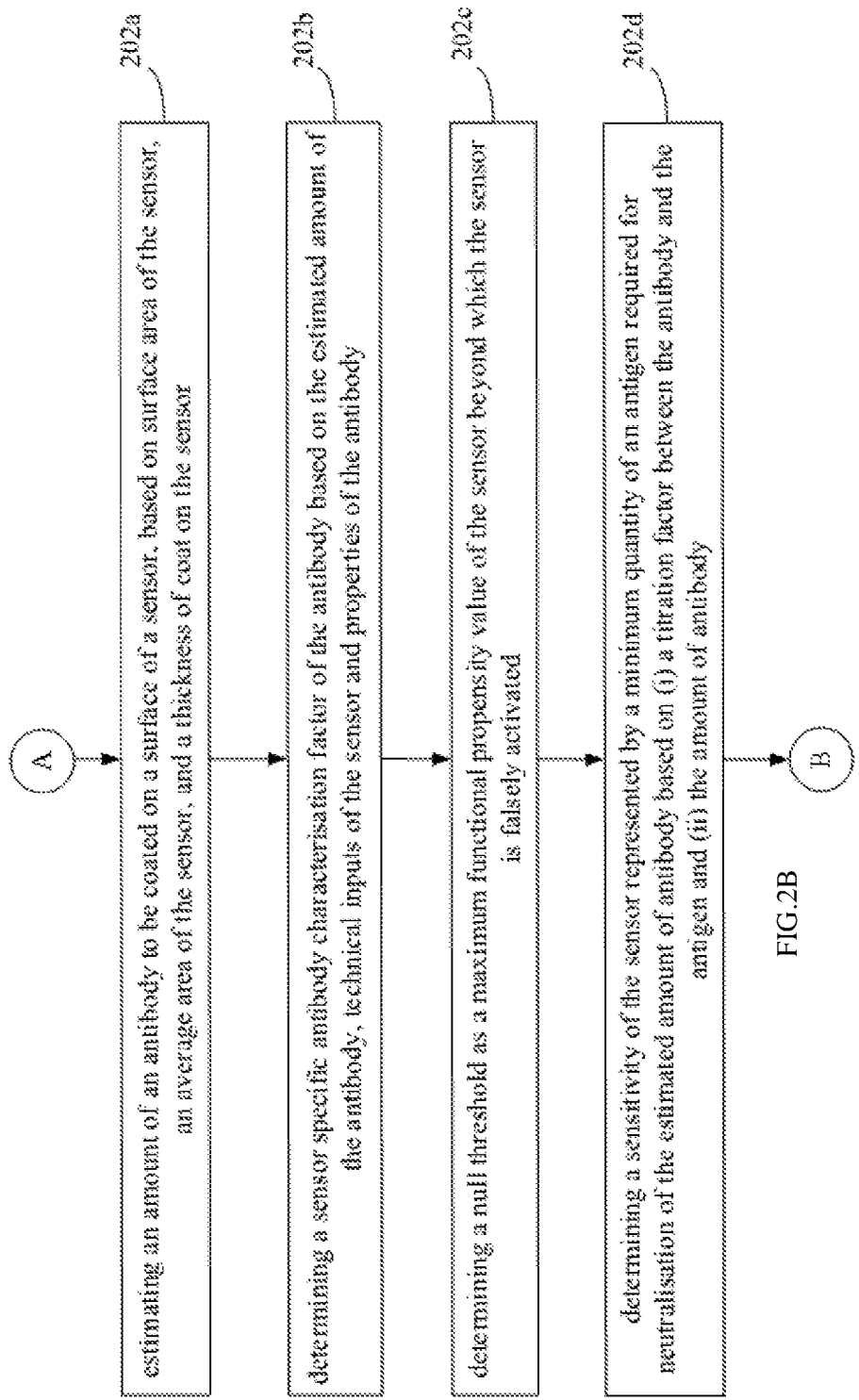
Figure 2C:
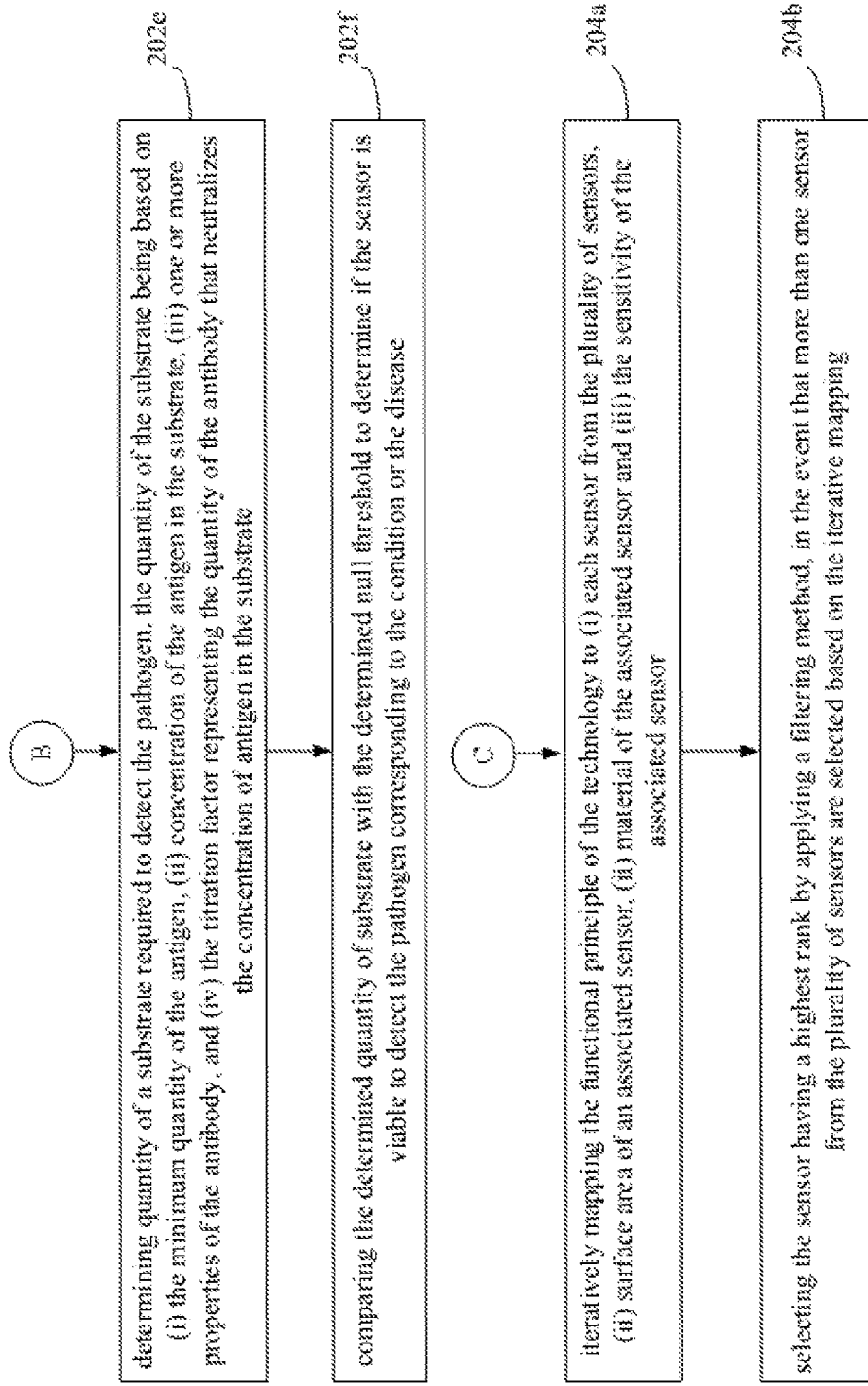

FIG. 2A through FIG. 2C illustrate an exemplary flow diagram of a computer implemented method 200 for detection of pathogens from a gaseous mixture associated with secretions, in accordance with some embodiments of the present disclosure. In an embodiment, the system 100 includes one or more data storage devices or memory 102 operatively coupled to the one or more hardware processors 104 and is configured to store instructions configured for execution of steps of the method 200 by the one or more hardware processors 104. The steps of the method 200 will now be explained in detail with reference to the components of the system 100 of FIG. 1. Although process steps, method steps, techniques or the like may be described in a sequential order, such processes, methods and techniques may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

In an embodiment of the present disclosure, the one or more hardware processors 104, are configured to determine, at step 202, one or more viable sensors to detect a pathogen corresponding to a condition or a disease under observation. The disease under observation may be COVID-19, SARS, MERS, and the like. In accordance with the present disclosure, the condition under observation may be a defect, an allergy, an exposure to say X-ray, and the like.

In accordance with the present disclosure, presence of pathogens in biological materials or substrates other than secretions may also be detected using the method 200 of the present disclosure. The method 200 may be used for testing or validating the presence of pathogen (as a constituent or a contaminant) in the substrate. The vaccine or broth may be converted to say an aerosol or a droplet form for use with the system 100 described herein.

The step of determining one or more viable sensors comprises performing iteratively, via the one or more hardware processors 104, steps *202a* through *202f* on each sensor from a plurality of sensors. In an embodiment, at step *202a*, an amount Q of an antibody to be coated on a surface of a sensor is estimated based on surface area A of the sensor, an average area α of the sensor, and a thickness T of coat on the sensor. At step *202b*, a sensor specific antibody characterisation factor X of the antibody is determined based on the estimated amount Q of the antibody, technical inputs of the sensor and properties of the antibody. At step *202c*, a null threshold Ø is determined as a maximum functional propensity value of the sensor beyond which the sensor is falsely activated. At step *202d*, a sensitivity of the sensor represented by a minimum quantity $Q_{ag}$ of an antigen required for neutralisation of the estimated amount Q of antibody is determined based on (i) a titration factor R between the antibody and the antigen and (ii) the amount Q of antibody. At step *202e*, quantity $Q_s$ of a substrate required to detect the pathogen is determined, the quantity $Q_s$ of the substrate being based on (i) the minimum quantity $Q_{ag}$ of the antigen, (ii) concentration C–ag of the antigen in the substrate, (iii) one or more properties x of the antibody, and (iv) the titration factor R representing the amount of the antibody that neutralizes the concentration C–ag of the antigen in the substrate. Finally, the determined quantity $Q_s$ of substrate is compared with the determined null threshold Ø to determine if the sensor is viable to detect the pathogen corresponding to the condition or the disease.

In accordance with an embodiment of the present disclosure, the step 202 of determining one or more viable sensors is preceded by obtaining an ontology of a plurality of inputs. In an embodiment, the system 100 may be configured to create the ontology of the plurality of inputs. In another embodiment, the system 100 may be configured to receive the ontology of the plurality of inputs. In accordance with the present disclosure, the plurality of inputs comprise: a) pathogen-oriented inputs, b) technology-oriented inputs, c) processing-oriented inputs pertaining to each antibody from the plurality of antibodies and each sensor from the plurality of sensors, and d) detection-oriented inputs pertaining to detection of the pathogen.

In an embodiment, the pathogen-oriented inputs include (i) inputs pertaining to a plurality of antigens, each antigen in the plurality of antigens being a target antigen corresponding to the condition or the disease; and (ii) inputs pertaining to a plurality of antibodies, each antibody in the plurality of antibodies corresponding to a target antigen in the plurality of antigens. In an embodiment, the inputs pertaining to the plurality of antigens may include a) nature of the pathogen (e.g. bacteria, virus, pollen, hapten, spores, and the like), b) nature of spread of the pathogen (e.g. air, droplet nucleus, insect vector, and the like), c) detectable and potent antigens on the pathogen, d) viability of binding capability of the antigen with the antibody in changing conditions of temperature and humidity. Typically, target antigen is the most potent and stable antigen known.

In an embodiment, the inputs pertaining to the plurality of antibodies may include a) available antibodies (stable and replicable immunoglobins) against the most stable and potent antigens. For each antibody, its physical properties, chemical properties, immunochemical properties, electrochemical properties and fluorescence, radiation, photochemistry or optometric characteristics may be received as part of the plurality of inputs. The physical properties may include molecular weight, density (number of molecules per microgram), molecular surface area, melting point, coagulation point and burning or combustion point, and the like. The chemical properties may include water solubility, organic solvent solubility, complex solvent solubility, litmus reaction, Oxidation index, Reduction Index, Coboxination Index, Ionization index, and the like. The immunochemical properties may include immune-valency or number of neutralized antigen molecules by an antibody. The electrochemical properties may include conductivity—plain and labeled (with metal and non-metal), electrical impedance or electrogenesis (voltage or current generated or blocked), and the like. fluorescence, radiation, photochemistry or optometric characteristics may include i) binding with fluorescent materials—intensity of fluorescence, time, temperature and other conditions required in neutralized or non-neutralized form; ii) radiation emission from the antibody including native radioactivity, if any, labeled with radioactive isotope (non-neutralized form), labeled with radioactive isotope (neutralized form); iii) photochemistry effect including any change in wavelength of light of reflection or refraction through an antibody smear (non-neutralized form to a neutralized form), any change in light related property of the antibody from non-neutralized form to a neutralized form like refractive index, opacity or turbulence, rotation of polarized light beam, prism effect or lens effect, and the like.

The use of technology is based upon type of substrate and the nature or state of the material used as an input. For instance, a material like vomitus which is acrid in nature and has a high electrical conductivity does not allow use of electro-chemistry-based technology and hence photo-recognition or nano-chain reaction-based nano-devices are feasible. Another example, when the input material contains heavy pathogens like pollens, the preferred sensor is cantilever or electrical impedance. The inputs related to the functional principle may include the primary functional principle that activates the sensor. For instance, a cantilever is activated by gravity, an electrode by conductivity, fluorescence by photochromism, and the like. The functional property may further include properties of the antibody that influences the sensor function or the state of the substrate that the sensor technology can consume. The technical inputs of each sensor may include the functional or binding area available on the sensor, a least count of the sensor, and the like. The least count represents least output value the sensor can produce as an output, for instance, for a cantilever sensor, a minimum deflection produced on activation represents its least count.

The processing-oriented inputs pertaining to each antibody may include a process of binding of the antibody to the sensor, a process of sensing of the activated sensor after exposure, secondary components required (other chemical components including solvents and binders), a process of standardization of binding antibodies on the sensor, quality assurance and quality assurance parameters, sensing exposure, post exposure process, and the like.

The detection-oriented inputs may include design characteristics and/or amount needed for various aspects including one or more of sample state, consumption state, state conversion, the antibody, immobilization agent, substrate, reaction state, temperature change, catalyst, intermediate agent, wash or flush, reaction time, interpretation, and the like.

In accordance with the present disclosure, having determined one or more viable sensors at step 202 using the ontology of the plurality of inputs described above, the one or more hardware processors 104, are configured to select a sensor, at step 204, from the determined one or more viable sensors. In an embodiment, the step of selecting a sensor involves iteratively mapping, at step 204a, the functional principle of the technology to (i) each sensor from the plurality of sensors, (ii) surface area of an associated sensor, (ii) material of the associated sensor and (iii) the sensitivity of the associated sensor. In the event that there is more than one sensor identified post the mapping, a sensor having a highest rank is selected, at step 204b, by applying a filtering method. The criteria for ranking may be either technical, business or a combination thereof. The technical criteria include the parameters mentioned for the mapping step. The business criteria may include cost of fabrication, average life, cost of associated measuring circuit or device, total cost of ownership, and the like.

In an embodiment, along with the three mapping parameters mentioned in step 204a, further mapping with a binding material for binding the antibody to the sensor may also be performed.

In accordance with an embodiment of the present disclosure, the step 202a of estimating amount Q of an antibody is represented as:

$$Q = \lim A(\alpha 1 - \alpha n) + (A \times \lambda q) + (\pi T), \text{ wherein}$$

A=surface area of the sensor,
$\alpha$=average area of the sensor,
$\lambda$=coefficient of chemical binding of the antibody, and wherein the antibody is either plain or labelled, for instance gold is the label for a gold labeled antibody,
q=quantity of the binding material,
$\pi$=Constant of binding associated with a binding between (i) the material of the associated sensor and the binding material or (ii) the material of the associated sensor and the antibody, in the embodiment where there is no binding material,
T=Thickness of the coat of the antibody with the binding material or the antibody only, in the embodiment where there is no binding material, and
n=number of sample sensors (considered to make up for variations between sensors of the same type) for each type of sensor.

In accordance with an embodiment of the present disclosure, the null threshold Ø, determined at step 202c, is represented as Ø=lim(B×X), wherein B=dLC/dΔ, LC being a least count of the sensor and Δ being a minimum delta of a response by the sensor when activated. To understand the minimum delta, consider a cantilever sensor. The cantilever sensor has a baseline value of deflection and a new value of deflection after the antibody and/or the binding material is added. The minimum deflection that is observed after addition of the antibody and/or the binding material represents the minimum delta.

In accordance with an embodiment of the present disclosure, the quantity $Q_s$ of the substrate determined at step 202e, is represented as $Q_s = \lim(Q_{ag} \times C - ag + x \times R)$, wherein $Q_{ag} = Q \times R$.

In accordance with the present disclosure, once the sensor is selected for detecting the pathogen, a gaseous mixture associated with a secretion is collected into the gas collection unit 108 of the system 100, at step 206, for detecting the pathogen, wherein the secretion is the substrate for the pathogen, and wherein the system is configured to include the selected sensor coated with the estimated amount Q of the antibody corresponding to the target antigen further corresponding to the condition or the disease under observation. Further, the pathogen in the collected gaseous mixture, is detected, at step 208, by the selected sensor based on an outcome of a reaction between the antigen and the antibody.

In certain cases, depending upon the physical chemistry of antigens and antibodies and the concentration of the detectable material in the substrate, the sensor may be a combination of more than one sensor of the same type using one or more types of antibodies. For instance, for detecting pathogen associated with Covid-19, the sensor may comprise three sub-sensors coated with Spike and nucleocapsid proteins in monoclonal and polyclonal versions. Alternatively, different types of sensors may be employed again having the same antibody or different antibodies on each of the sensors. Accordingly, in an embodiment of the present disclosure, the sensor comprises (i) two or more of the selected sensor having one or more types of antibodies therein or (ii) two or more of the determined one or more viable sensors, each of the two or more sensors having one or more types of antibodies therein.

In accordance with an embodiment of the present disclosure, the detected pathogen may be quantified, via the one or more hardware processors, at step 210, based on a quantum of the outcome of the reaction between the antigen and the antibody using (i) the minimum quantity $Q_{ag}$ of the antigen required for neutralisation of the estimated amount of antibody and result in an outcome (e.g. deflection in case of a cantilever sensor, blocked current in case of electrical impedance, and the like) and (ii) a maximum quantity of the antigen beyond which the outcome does not change. Typically, the quantifying is done by comparing the outcome of the reaction against a known calibration information like a graph or by calculating using a titration formula.

Figure 3:
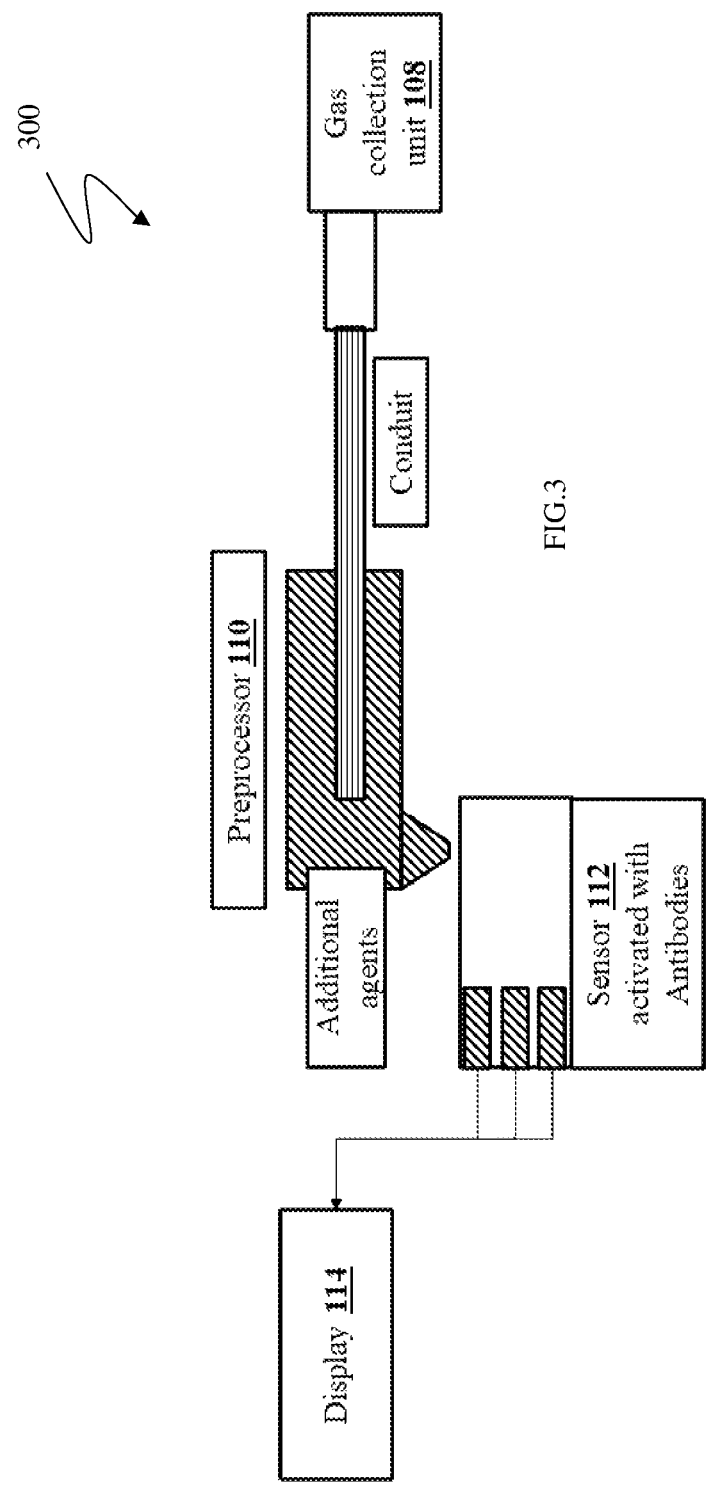
FIG. 3 is an exemplary representation of a device for detection of pathogens from a gaseous mixture associated with secretions, according to some embodiments of the present disclosure.

In an aspect of the present disclosure, there is provided a device for detecting a pathogen corresponding to a condition or a disease under observation. FIG. 3 is an exemplary representation of a device 300 for detection of pathogens from a gaseous mixture associated with secretions, according to some embodiments of the present disclosure. In an embodiment, the device comprises: the gas collection unit 108 configured to collect a gaseous mixture associated with a secretion, wherein the secretion is the substrate for the pathogen; the sensor 112 coated/activated with an estimated amount of an antibody corresponding to a target antigen that further corresponds to the condition or the disease; wherein the pathogen in the collected gaseous mixture is detected based on an outcome of a reaction between the target antigen and the antibody. Optionally, the preprocessor 110 configured to preprocess the collected gaseous mixture received via the gas collection unit (and optionally a conduit) may be provided such that the pathogen contained in the collected gaseous mixture is released. Again, the display 114 configured to provide the outcome indicative of at least one of (i)

the presence or absence of the pathogen and (ii) quantitative information of the detected pathogen may be provided.

Figure 4:
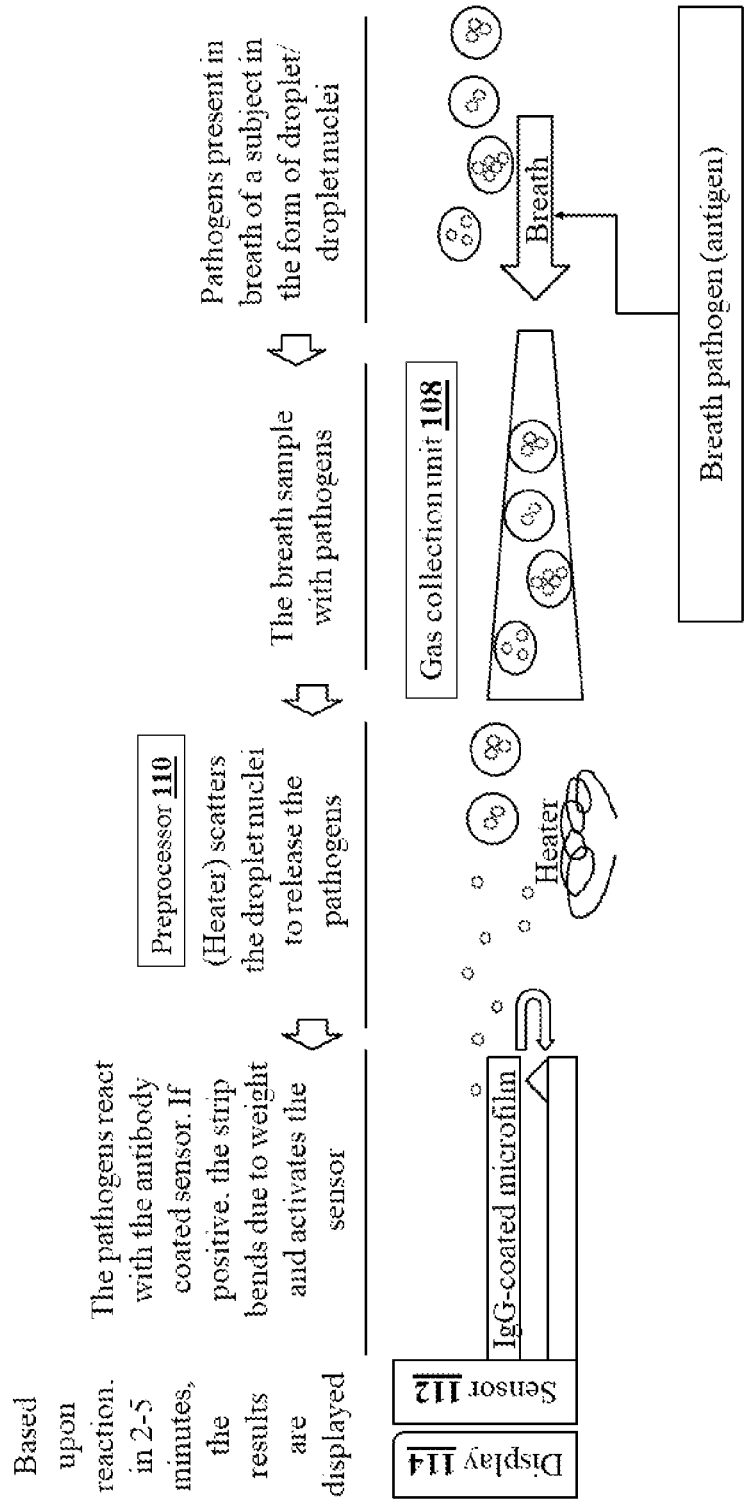
FIG. 4 is a functional flow diagram for detection of pathogens from a gaseous mixture associated with secretions, according to some embodiments of the present disclosure.

FIG. 4 is a functional flow diagram for detection of pathogens from a gaseous mixture associated with secretions according to some embodiments of the present disclosure. Although FIG. 4 is an exemplary representation of a gaseous mixture being breath of a subject being monitored, it may be understood by those skilled in the art that the described functional flow and the system 100 are applicable to any form of gaseous mixture containing potential antigens to be tested based on a corresponding antibody coated on the sensor 106 for detecting the antigen upon there being an antigen-antibody reaction and the FIG. 4 is a non-limiting embodiment provided for explanation of the functional flow. Accordingly, in the illustrated embodiment, a breath sample of a subject being monitored in the form of a droplet nuclei is captured in the gas collection unit 108, represented by a conical tube (exemplary illustration). The preprocessor 110, represented by a heater coil is used to break the droplet nuclei and release the pathogens. The sensor 112 is represented by an Immunoglobulin, (preferably an antibody mix of the spike protein or nucleocapsid protein of a virus or bacteria or the anti-surface-antigen antibody for hapten which can be natural or synthetic polyclonal or monoclonal antibodies) coated microfilm or electrode or any other sensor enabling the process of detection through various methods including but not limited to current generation or amendment, fluorescence, electrical impedance, state change, circuit completion, photoelectric changes or the like. IgG is an exemplary antibody used in the illustrated embodiment of FIG. 4. The amount of the antibody and the selection on the sensor are based on the various computations described with reference to FIG. 2. The pathogen in the preprocessed breath sample reacts with the antibody on the microfilm. In the event of antigen-antibody reaction, an outcome may be output to the display 114.

Thus, it may be noted from the above description that the device and method of the present disclosure provides an early outcome (within few minutes) as compared to the state-of-the-art wherein a reliable outcome takes hours (or days) or even multiple screenings. Since the present disclosure provides the sensor equipped with a condition or a disease specific antibody, and is sensitive in very small quantities, the presence of a pathogen can be detected even before the immune reaction sets up, when the subject may be asymptomatic. State-of-the-art works with the antigen being part of the device and the antibody being captured from the subject being monitored. In many cases, an infection has to be incubated long enough for the development of antibody in the serum, implying the subject has already been infected for that time period and also is a potential contagion. Early detection can yield several advantages not limited to preventing spread of the detected pathogen associated disease, timely intervention for treating the subject, as needed, reduced costs involved in the manufacture and usage of the method and device of the present disclosure.

The method of the present disclosure requires practically no skilled intervention and produces an accurate and specific output without imposing risk to the persons involved including healthcare professionals. Since the gaseous mixture used is a small sample, in the event of presence of pathogens, the antibody used as part of the sensor is sufficient to ensure there is no risk of exposure to the healthcare professional. Furthermore, since gaseous mixtures associated with secretions obtained in their routine disposal state are used, there is no tissue handling involved.

It may be further noted by those skilled in the art that the method and device of the present disclosure neither depends upon the body's immune response nor upon component analysis-based reactions. Some state-of-the-art techniques that utilize antibodies or deal with gaseous mixtures include pregnancy detection, breath analyzers and odor detectors. Pregnancy detection involves detection of organic compound (hormone), is based on hormone-antibody reaction and needs a high concentration of soluble form of hormone for the detection. Breath analyzers are dependent on the chemical signature of the material, for instance, alcohol, ammonia, hydrogen sulphide, etc. and are therefore gas chromatography based and not antibody-antigen based as is the case with the present disclosure. The antibody used in odor detectors are chemical antibodies created to detect volatile organic chemicals. The technology used in odor detectors is capable of binding the chemical antibodies to the organic chemical materials only, which are not pathogenic in nature. Thus, pathogens in the form of say, droplet nuclei cannot be detected by any of the prevalent methodologies or associated hardware.

The state-of-the-art uses two types of materials as chemical alternatives to immunoglobulin antibodies, viz. designed antibodies or chemicals that has shown affection for the antigen other than the immunoglobulin. This material use pertains to the limitation of immunoglobulins with respect to their properties in use in nanosensors. However, these alternate chemicals have properties of binding to several other materials hence have low specificity. Often, the design of the antibodies which are not tested to work in different environmental and physical conditions tend to change their sensitivity. Hence, the immunoglobulins which are unconditionally sensitive and specific to the target antigen are only correctly detected in the art.

Domain understanding of pathogenesis or of nanosensor-physics has limitations in generating relationships of the immunoglobulins or natural antibodies which do not give liberty of design changes in either elements (sensors or immunoglobulins). Hence, to identify the association of these two components of the un-amendable elements of say, breath analysis, the present disclosure provides equations and formulae that use domain knowledge only as a ontology and generates a mathematical representation of the relationship of a sensor with the immunoglobulin. On the contrary, current designing aspects are highly dependent upon using designed antibodies with or without redesigning of the sensors based upon domain knowledge.

Furthermore, the state-of-the-art technologies for gaseous mixtures are based on organic chemical detection, which is not necessarily a pathogen. The method and system of the present disclosure detect the pathogen and not associated chemicals like toxins, metabolites and disease-related secretions.

The written description describes the subject matter herein to enable any person skilled in the art to make and use the embodiments. The scope of the subject matter embodiments is defined herein and may include other modifications that occur to those skilled in the art. Such other modifications are intended to be within the scope of the present disclosure if they have similar elements that do not differ from the literal language of the present disclosure or if they include equivalent elements with insubstantial differences from the literal language of the embodiments described herein.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more hardware processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, non-volatile memory, hard drives, CD ROMs, DVDs, flash drives, disks, and any other known physical storage media.

It is intended that the disclosure and examples be considered as exemplary only, with a true scope of disclosed embodiments being indicated by the following claims.

The invention claimed is:

1. A processor implemented method comprising the steps of:
   determining, via one or more hardware processors, one or more viable sensors to detect a pathogen corresponding to a condition or a disease, the step of determining comprising:
   performing iteratively, via the one or more hardware processors, on each sensor from a plurality of sensors the followings steps:
      estimating an amount Q of an antibody to be coated on a surface of a sensor, based on surface area A of the sensor, an average area a of the sensor, and a thickness T of coat on the sensor;
      determining a sensor specific antibody characterisation factor X of the antibody based on the estimated amount Q of the antibody, technical inputs of the sensor and one or more properties x of the antibody;
      determining a null threshold Ø as a maximum functional propensity value of the sensor beyond which the sensor is falsely activated;
      determining a sensitivity of the sensor represented by a minimum quantity $Q_{ag}$ of an antigen required for neutralisation of the estimated amount Q of antibody based on (i) a titration factor R between the antibody and the antigen and (ii) the amount Q of the antibody;
      determining quantity $Q_s$ of a substrate required to detect the pathogen, the quantity $Q_s$ of the substrate being based on (i) the minimum quantity $Q_{ag}$ of the antigen, (ii) concentration C–ag of the antigen in the substrate, (iii) the one or more properties x of the antibody, and (iv) the titration factor R representing the amount of the antibody that neutralizes the concentration C−ag of the antigen in the substrate; and comparing the determined quantity $Q_s$ of substrate with the determined null threshold Ø to determine if the sensor is viable to detect the pathogen corresponding to the condition or the disease.

2. The processor implemented method of claim 1, wherein the step of determining one or more viable sensors is preceded by obtaining an ontology of a plurality of inputs comprising:

a) pathogen-oriented inputs including:

(i) inputs pertaining to a plurality of antigens, each antigen in the plurality of antigens being a target antigen corresponding to the condition or the disease; and (ii) inputs pertaining to a plurality of antibodies, each antibody in the plurality of antibodies corresponding to a target antigen in the plurality of antigens;

b) technology-oriented inputs including:

(i) inputs related to a functional principle of a technology that activates a sensor from the plurality of sensors; and (ii) technical inputs of each sensor from the plurality of sensors;

c) processing-oriented inputs pertaining to each antibody from the plurality of antibodies and each sensor from the plurality of sensors; and d) detection-oriented inputs pertaining to detection of the pathogen.

3. The processor implemented method of claim 2, further comprising selecting a sensor, via the one or more hardware processors, from the determined one or more viable sensors, the step of selecting comprising:
iteratively mapping the functional principle of the technology to (i) each sensor from the plurality of sensors, (ii) surface area of an associated sensor, (ii) material of the associated sensor and (iii) the sensitivity of the associated sensor; and
selecting the sensor having a highest rank by applying a filtering method, in the event that more than one sensor from the plurality of sensors are selected based on the iterative mapping.

4. The processor implemented method of claim 3, wherein the step of iteratively mapping involves further mapping with a binding material for binding the antibody to the sensor.

5. The processor implemented method of claim 3, wherein the step of estimating amount Q of an antibody is represented as:

$$Q = \lim A(\alpha 1 - \alpha n) + (A \times \lambda q) + (\pi T), \text{ wherein}$$

A=surface area of the sensor,
α=average area of the sensor,
λ=coefficient of chemical binding of the antibody, and wherein the antibody is either plain or labeled,
q=quantity of the binding material,
π=Constant of binding associated with a binding between (i) the material of the associated sensor and the binding material or (ii) the material of the associated sensor and the antibody,
T=Thickness of the coat of the antibody with the binding material or the antibody, and
n=number of sample sensors for each type of sensor.

6. The processor implemented method of claim 3, wherein the null threshold Ø is represented as Ø=lim (B×X), and wherein B=dLC/dΔ, LC being a least count of the sensor and Δ being a minimum delta of a response by the sensor when activated.

7. The processor implemented method of claim 3, wherein the quantity $Q_s$ of the substrate is represented as $Q_s$=lim ($Q_{ag}$×C−ag+x×R), and wherein $Q_{ag}$=Q×R.

8. The processor implemented method of claim 3, further comprising:
collecting a gaseous mixture associated with a secretion into a gas collection unit of a system for detecting the pathogen, wherein the secretion is the substrate for the pathogen, and wherein the system is configured to include the selected sensor coated with the estimated amount of the antibody corresponding to the target antigen further corresponding to the condition or the disease; and
detecting, by the selected sensor, the pathogen in the collected gaseous mixture based on an outcome of a reaction between the antigen and the antibody.

9. The processor implemented method of claim 8, further comprising quantifying, via the one or more hardware processors, the detected pathogen based on a quantum of the outcome of the reaction between the antigen and the antibody using (i) the minimum quantity $Q_{ag}$ of the antigen required for neutralisation of the estimated amount of antibody and result in an outcome and (ii) a maximum quantity of the antigen beyond which the outcome does not change.

10. A system comprising: one or more data storage devices operatively coupled to one or more hardware processors and configured to store instructions for execution via the one or more hardware processors, said one or more hardware processors programmed to:

determine one or more viable sensors to detect a pathogen corresponding to a condition or a disease, by performing iteratively on each sensor from a plurality of sensors, the followings steps:

estimating, an amount Q of an antibody to be coated on a surface of a sensor, based on surface area A of the sensor, an average area a of the sensor, and a thickness T of coat on the sensor; determining, a sensor specific antibody characterization factor X of the antibody based on the estimated amount Q of the antibody, technical inputs of the sensor and one or more properties x of the antibody;

determining, a null threshold Ø as a maximum functional propensity value of the sensor beyond which the sensor is falsely activated;

determining, a minimum quantity $Q_{ag}$ of an antigen required for neutralization of the estimated amount Q of antibody based on (i) a titration factor R between the antibody and the antigen and (ii) the amount Q of antibody;

determining, quantity of a substrate Qs required to detect the pathogen, the quantity Qs of the substrate being based on (i) the minimum quantity $Q_{ag}$ of the antigen, (ii) concentration C−ag of the antigen in the substrate, (iii) the one or more properties x of the antibody, and (iv) the titration factor R representing the amount of the antibody that neutralizes the concentration C−ag of the antigen in the substrate; and comparing the determined quantity Qs of substrate with the determined null threshold Ø to determine if the sensor is viable to detect the pathogen corresponding to the condition or the disease.

11. The system of claim 10, wherein the one or more hardware processors are configured to obtain, prior to determining the one or more viable sensors, an ontology of a plurality of inputs comprising:

a) pathogen-oriented inputs including:

(i) inputs pertaining to a plurality of antigens, each antigen in the plurality of antigens being a target antigen corresponding to the condition or the disease; and (ii) inputs pertaining to a plurality of antibodies, each antibody in the plurality of antibodies corresponding to a target antigen in the plurality of antigens;

b) technology-oriented inputs including:

(i) inputs related to a functional principle of a technology that activates a sensor from the plurality of sensors; and (ii) technical inputs of each sensor from the plurality of sensors;

c) processing-oriented inputs pertaining to each antibody from the plurality of antibodies and each sensor from the plurality of sensors; and d) detection-oriented inputs pertaining to detection of the pathogen.

12. The system of claim 11, wherein the one or more hardware processors are further configured to select a sensor from the determined one or more viable sensors by:

iteratively mapping the functional principle of the technology to (i) each sensor from the plurality of sensors, (ii) surface area of an associated sensor, (ii) material of the associated sensor and (iii) the sensitivity of the associated sensor; and selecting the sensor having a highest rank by applying a filtering method, in the event that more than one sensor from the plurality of sensors are selected based on the iterative mapping.

13. The system of claim 12, wherein the one or more hardware processors are configured to involve further mapping with a binding material for binding the antibody to the sensor.

14. The system of claim 12, wherein estimating amount Q of an antibody is represented as:

$$Q = \lim A(\alpha 1 - \alpha n) + (A \times \lambda q) + (\pi T), \text{ wherein}$$

A=surface area of the sensor,
α=average area of the sensor,
λ=coefficient of chemical binding of the antibody, and wherein the antibody is either plain or labeled,
q=quantity of the binding material,
π=Constant of binding associated with a binding between (i) the material of the associated sensor and the binding material or (ii) the material of the associated sensor and the antibody,
T=Thickness of the coat of the antibody with the binding material or the antibody, and
n=number of sample sensors for each type of sensor;
wherein the null threshold Ø is represented as Ø=lim (B×X), and wherein B=dLC/dΔ, LC being a least count of the sensor and Δ being a minimum delta of a response by the sensor when activated; and
wherein the quantity $Q_s$ of the substrate is represented as $Q_s = \lim (Q_{aq} \times C\text{-}ag + x \times R)$, and wherein $Q_{aq} = Q \times R$.

15. The system of claim 14, further comprising:
a gas collection unit configured to collect the gaseous mixture associated with a secretion, wherein the secretion is the substrate for the pathogen;
a sensor (112) being the selected sensor coated with the estimated amount of the antibody corresponding to the target antigen that further corresponds to the condition or the disease,
wherein the one or more hardware processors are configured to (i) detect the pathogen in the collected gaseous mixture based on an outcome of a reaction between the antigen and the antibody, and (ii) quantify the detected pathogen based on a quantum of the outcome of the reaction between the antigen and the antibody using (i) the minimum quantity $Q_{ag}$ of the antigen required for neutralisation of the estimated amount of antibody and result in an outcome and (ii) a maximum quantity of the antigen beyond which the outcome does not change.

16. The system of claim 15, further comprising one or more of:
a preprocessor configured to preprocess the collected gaseous mixture received via the gas collection unit such that the pathogen contained in the collected gaseous mixture is released; and
a display configured to provide the outcome indicative of at least one of (i) the presence or absence of the pathogen and (ii) quantitative information of the detected pathogen.

17. The system of claim 15, wherein the sensor comprises (i) two or more of the selected sensor having one or more types of antibodies therein or (ii) two or more of the determined one or more viable sensors, each of the two or more sensors having one or more types of antibodies therein.

18. A computer program product comprising a non-transitory computer readable medium having a computer readable program embodied therein, wherein the computer readable program, when executed on a computing device, causes the computing device to be programmed to:
determine one or more viable sensors to detect a pathogen corresponding to a condition or a disease, by performing iteratively on each sensor from a plurality of sensors, the followings steps:
estimating, an amount Q of an antibody to be coated on a surface of a sensor, based on surface area A of the sensor, an average area a of the sensor, and a thickness T of coat on the sensor; determining, a sensor specific antibody characterization factor X of the antibody based on the estimated amount Q of the antibody, technical inputs of the sensor and one or more properties x of the antibody; determining, a null threshold Ø as a maximum functional propensity value of the sensor beyond which the sensor is falsely activated;
determining, a minimum quantity $Q_{ag}$ of an antigen required for neutralization of the estimated amount Q of antibody based on (i) a titration factor R between the antibody and the antigen and (ii) the amount Q of antibody; determining, quantity of a substrate Qs required to detect the pathogen, the quantity Qs of the substrate being based on (i) the minimum quantity $Q_{ag}$ of the antigen, (ii) concentration C−ag of the antigen in the substrate, (iii) the one or more properties x of the antibody, and (iv) the titration factor R representing the amount of the antibody that neutralizes the concentration C−ag of the antigen in the substrate; and comparing the determined quantity Qs of substrate with the determined null threshold Ø to determine if the sensor is viable to detect the pathogen corresponding to the condition or the disease.

19. The computer program product of claim 18, wherein the computer readable program further causes the computing device to obtain, prior to determining the one or more viable sensors, an ontology of a plurality of inputs comprising:

a) pathogen-oriented inputs including:

(i) inputs pertaining to a plurality of antigens, each antigen in the plurality of antigens being a target antigen corresponding to the condition or the disease; and (ii) inputs pertaining to a plurality of antibodies, each antibody in the plurality of antibodies corresponding to a target antigen in the plurality of antigens;

b) technology-oriented inputs including:

(i) inputs related to a functional principle of a technology that activates a sensor from the plurality of sensors; and (ii) technical inputs of each sensor from the plurality of sensors;

c) processing-oriented inputs pertaining to each antibody from the plurality of antibodies and each sensor from the plurality of sensors; and d) detection-oriented inputs pertaining to detection of the pathogen.

20. The computer program product of claim 19, wherein the computer readable program further causes the computing device to select a sensor from the determined one or more viable sensors by:

iteratively mapping the functional principle of the technology to (i) each sensor from the plurality of sensors, (ii) surface area of an associated sensor, (ii) material of the associated sensor and (iii) the sensitivity of the associated sensor; and selecting the sensor having a highest rank by applying a filtering method, in the event that more than one sensor from the plurality of sensors are selected based on the iterative mapping.

\* \* \* \* \*